United States Patent [19]

Goodin et al.

[11] Patent Number: 4,723,938
[45] Date of Patent: Feb. 9, 1988

[54] SINGLE PLUNGER INFLATION DEVICE FOR ANGIOPLASTY CATHETER

[75] Inventors: Richard L. Goodin, Blaine; Mark A. Rydell, Golden Valley, both of Minn.

[73] Assignee: Schneider-Shiley (USA) Inc., Minneapolis, Minn.

[21] Appl. No.: 945,965

[22] Filed: Dec. 24, 1986

[51] Int. Cl.⁴ .............................................. A61M 29/00
[52] U.S. Cl. ........................................ 604/99; 604/97; 604/108; 604/100; 128/344
[58] Field of Search .................. 604/93, 96, 97, 98, 604/99, 100, 104, 107, 118, 207, 208, 211, 108, 227, 236; 128/303 R, 303.11, 344

[56] References Cited

U.S. PATENT DOCUMENTS

| | | | |
|---|---|---|---|
| 3,563,240 | 2/1971 | Silver | 604/211 |
| 4,275,729 | 6/1981 | Silver et al. | 604/211 |
| 4,312,343 | 1/1982 | LeVeen et al. | 604/211 |
| 4,413,989 | 11/1983 | Schjeldahl et al. | 604/96 |
| 4,439,185 | 3/1984 | Lundquist | 604/99 |
| 4,439,186 | 3/1984 | Kuhl | 604/99 |
| 4,583,974 | 4/1986 | Kokernak | 604/99 |
| 4,655,749 | 4/1987 | Fischione | 128/344 |

Primary Examiner—Barry S. Richman
Assistant Examiner—T. J. Wallen
Attorney, Agent, or Firm—Orrin M. Haugen; Thomas J. Nikolai; Frederick W. Niebuhr

[57] ABSTRACT

An inflation/deflation device for an angioplasty balloon catheter which permits quick inflation to an approximate working pressure followed by a fine but slower adjustment to a final desired pressure. The device includes a housing containing a syringe of the type having a cylindrical chamber containing a piston. A specially designed plunger extends from the proximal end of the housing whereby the initial approxiate pressure can be achieved by the hand-squeezing of the plunger and a slight rotation of that plunger is used to maintain the plunger in a locked disposition. An internal shaft is disposed within the tubular plunger and its distal end is secured to the syringe's piston. The internal shaft includes a threaded segment on its exterior surface engaging a correspondingly threaded surface on the interior of the plunger such that rotation of the shaft relative to the plunger causes axial movement of the piston within the syringe.

5 Claims, 5 Drawing Figures

U.S. Patent    Feb. 9, 1988    4,723,938
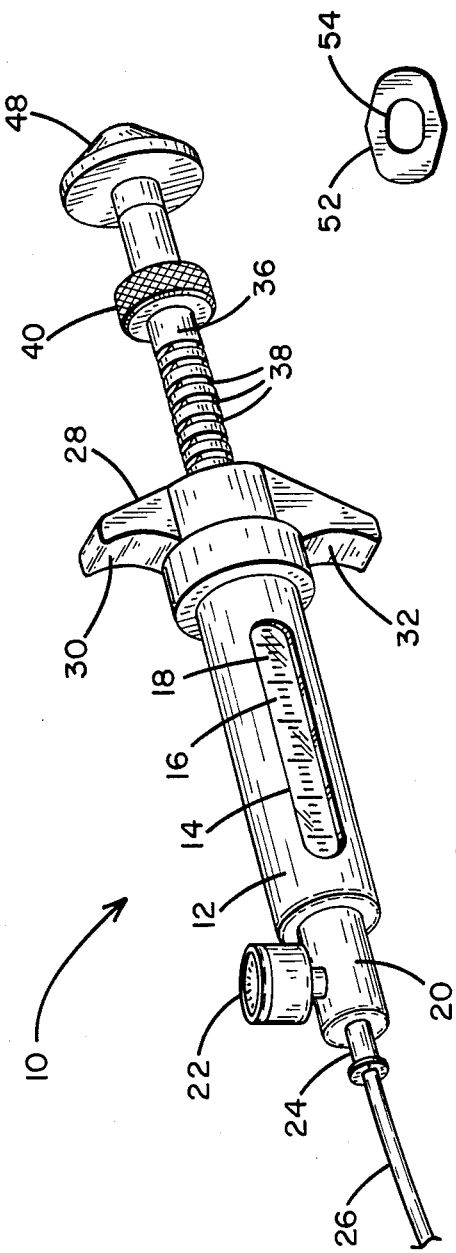
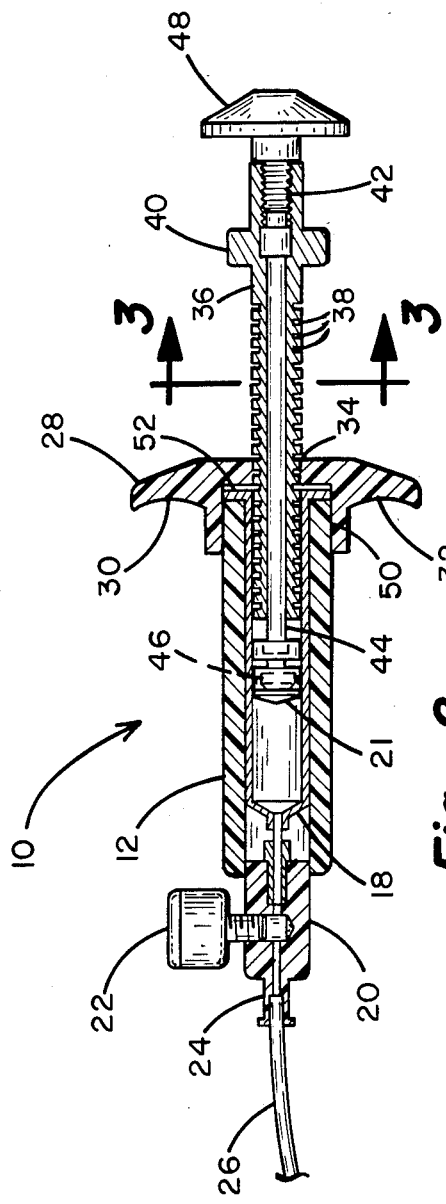
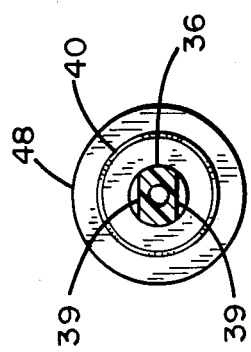
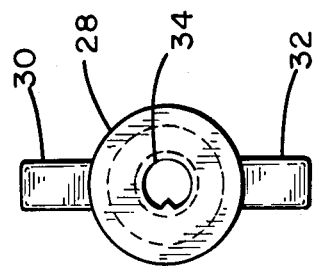

SINGLE PLUNGER INFLATION DEVICE FOR ANGIOPLASTY CATHETER

BACKGROUND OF THE INVENTION

I. Field of the Invention

This invention relates generally to apparatus for performing angioplasty procedures for opening partially occluded blood vessels, and more particularly to a hand-operated inflation and fluid dispensing device adapted to be connected to the proximal end of an angioplasty catheter for either inflating the expander member on that catheter or supplying a radiopaque contrast medium through the catheter and out its distal end.

II. Discussion of the Prior Art

There is described in the Schjeldahl et al U.S. Pat. No. 4,413,989 the configuration of an angioplasty catheter specifically adapted to treat stenotic lesions located in one of the coronary arteries. Basically, the catheter comprises an elongated tubular member having a non-distensible expander member disposed proximate its distal end, the expander member being inflatable by introducing a fluid through the proximal end of the catheter whereby it flows through the lumen of the catheter and out one or more ports in the side wall of the tubular member which are surrounded by the expander member.

In treating stenotic lesions, it is often necessary to pressurize the expander member to a pressure in the range of from 7 to 10 atmosphere or more. This pressure must be sustained for periods of up to 30 seconds or more.

There is currently on the market an angioplasty catheter inflation device in the form of a molded plastic housing configured to contain a hypodermic-type syringe having a diameter of about 6.5 cms. and whose output port is coupled to the proximal end of the tubular catheter body. The plunger of the syringe is suitably positioned relative to integrally molded finger grips on the housing so that the plunger will fit in the palm of the hand as the user's fingers wrap about the finger grips. By squeezing, fluid is ejected from the syringe and through the elongated catheter so as to inflate the expander member. The device is constructed in accordance with the Lundquist U.S. Pat. No. 4,439,185 assigned to Advanced Cardiovascular Systems, Inc. of Mountain View, Calif. Using this prior art device, however, it is extremely difficult for the cardiologist or technician to sustain the necessary pressures for the time interval during which the expander is pressurized. It requires a very strong grip and often it is difficult to hold the device steady and at the desired inflation pressure due to the strong force which must be applied to the inflation device. While the applied force can be reduced by reducing the overall diameter of the syringe's piston, this necessarily reduces the volume of fluid available to, for example, initially fill the lumen of the catheter and the expander with fluid or to later inject contrast media when the site being treated is to be inspected using fluoroscopic techniques.

Described in the Kokernak U.S. Pat. No. 4,583,974 is an inflation syringe for a balloon catheter which has a cylindrical body in which a tubular glass cylinder is enclosed. A movable plunger is disposed within the glass cylinder and is attached to a threaded shaft extending outwardly from one end of the syringe. A threaded latch member is pivotally secured to the body for selectively engaging the threads on the movable plunger. When the latch member is engaged with the threaded shaft, rotation of the shaft results in a controlled incremental axial movement of the plunger and a corresponding increase or decrease in the hydraulic pressure within the catheter system. When the latch is disengaged, however, the shaft is free to move axially, allowing quick deflation of the angioplasty balloon.

SUMMARY OF THE INVENTION

Certain of the drawbacks of the prior arrangements described above are obviated by the angioplasty catheter inflation/deflation device of the present invention. It comprises a molded plastic tubular body or housing dimensioned to contain within the bore thereof a hypodermic style syringe having an elastomeric plunger or piston contained within the bore thereof and a piston rod extending outwardly therefrom. The piston rod is also tubular and has a pattern of notches or grooves longitudinally spaced therealong. The grooved surface is also flattened along two diametrically opposed chords so as to be able to pass through a generally oval aperture formed in a flange plate secured to one end of the tubular body housing. The bore of the tubular housing is also threaded internally over a portion of its surface and a coaxially disposed rod having the piston attached to one end thereof and externally disposed threads proximate the other end thereof for mating with the internally threaded surface of the main plunger shaft. A palm-engaging knob is secured to the proximal end of the center shaft.

By appropriately orienting the main plunger shaft relative to the oval opening in the end flange of the housing, an axially directed force causes the piston plunger to be moved distally to force the fluid out of the syringe. A slight rotation of the main plunger shaft, however, causes that shaft to be locked relative to the housing to maintain a desired pressure. The pressure can be increased or decreased by rotating the knob on the proximal end of the central shaft, advancing or retracting the position of the plunger due to the threaded engagement between the main plunger shaft and its concentrically disposed center shaft. The hydraulic pressure can be relieved by merely again slightly rotating the main plunger shaft so that it is appropriately aligned with the oval aperture in the end flange and pulling back on the main plunger.

OBJECTS

It is accordingly a principal object of the present invention to provide an improved inflation syringe for use with an angioplasty catheter.

Another object of the invention is to provide a relatively low-cost, disposable inflation/deflation device for use with an angioplasty catheter.

A still further object of the invention is to provide an inflation/deflation device for an angioplasty catheter which allows the physician to readily bring the balloon pressure to a desired value and for rapidly drawing a vacuum in the balloon when desired.

A yet further object of the invention is to provide an inflation/deflation device for an angioplasty catheter in which an operating pressure, once achieved, can be maintained without undue physical effort on the part of the surgeon.

These and other objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE DRAWINGS

FIG. 1 is a perspective view of the inflation/deflation device of the present invention;

FIG. 2 is a longitudinal cross-sectional view of the device of FIG. 1;

FIG. 3 is a cross-sectional view of the main plunger shaft taken along line 3—3 in FIG. 2;

FIG. 4 is a detailed drawing of the body end flange; and

FIG. 5 is an end view of the handle end cap member.

DESCRIPTION OF THE PREFERRED EMBODIMENT

Referring to FIG. 1, the inflation/deflation syringe apparatus for a balloon catheter is indicated generally by numeral 10 and is seen to include a generally tubular housing 12 which is preferably formed in a molding process from a suitable plastic material. An elongated slot or opening 14 is formed through the side wall of the housing, allowing the user to view the graduated markings 16 formed on the exterior surface of a tubular syringe 18 contained within the bore of the housing 12. The tubular syringe is quite conventional and includes a cylindrical chamber in which is disposed a reciprocally movable piston member 20 (FIG. 2) which is formed of an elastomeric material and dimensioned so as to provide a seal with the side walls of the cylindrical chamber.

Affixed to the distal end of the housing 12 is a mounting manifold 20 which supports a pressure measuring gauge 22, placing it in fluid communication with the outlet of the syringe 18 and with a Luer fitting 24 to which a balloon catheter 26 may be secured.

An end-cap 28, having radially projecting finger grips 30 and 32 for accommodating the index finger and middle finger of the user, is attached to the proximal end of the housing 12.

Referring next to FIGS. 2 and 3, there is seen exiting from an aperture 34 formed in the end of the end cap 28 a tubular main plunger 36. Formed along the length of the tubular body of the main plunger 36 is a series of annular grooves, as at 38, each being generally equally spaced from one another. As can be seen in the cross-sectional view of FIG. 3, the cross-section of the main plunger 36 is not circular but, instead, is flattened along two diametrically opposed chords 39 of equal length. The tubular main plunger 36 is preferably formed in a molding operation and, as such, is formed to include a coaxially disposed, integrally formed cylindrical enlargement 40 which is preferably knurled about its periphery to facilitate gripping with the fingers.

Internal threads 42 are formed on the inside diameter of the tubular main plunger 36 and an elongated shaft 44, having corresponding external threads on its mating end portion, is fitted into the bore of the plunger 36 with the distal end of the shaft 44 being joined by a coupling member 46 to the elastomeric piston 20 of the syringe 18.

A knob 48 is affixed to the proximal end of the elongated shaft 44 and by rotating same in a clockwise direction while holding the knob 40 against rotation, the piston 20 will be displaced in the distal within its cylindrical chamber. Similarly, a counterclockwise rotation of the knob 48 while maintaining the tubular main plunger 36 stationery results in a displacement of the piston 20 in the proximal direction.

Located in a recess formed about the counterbore 50 of the end cap 28 is a metal flange 52, the shape of which, by reference to FIG. 3, is best seen in FIG. 4. The flange is seen to include a centrally disposed aperture 54 which is noncircular and which is seen to conform generally to the crosssectional shape of the tubular main plunger 36 in the zone occupied by the annular grooves 38. Thus, when the grooved body portion of the tubular main plunger 36 is properly aligned with the aperture 54, it can be advanced into the bore of the housing 12 by pressing on the knob 48 and because of the described threaded engagement between the main plunger 36 and the centrally disposed shaft 44, the piston 20 will move along with the tubular plunger. By rotating the tubular plunger, however, as by turning the knurled knob 40 slightly in either the clockwise or the counterclockwise direction, the main plunger will become locked against axial movement relative to the housing 12 by the engagement of the walls of one of the grooves 38 with the edge of the surface defining the non-circular opening in the flange plate 52.

Thus, it can be seen that the balloon (not shown) on the catheter 26 may be inflated to a predetermined pressure as measured by the gauge 22 by gripping the finger grips 30 and 32 with the index and middle fingers of the hand while the palm of the hand is used to press on the knob 48. Once the catheter and balloon have been filled and a modest pressure is reached, the physician, by rotating the knob 40, can lock the piston against longitudinal movement within the syringe. To bring the balloon to the desired working pressure, the physician then rotates the knob 48 which screws the internal shaft 44 inward and forces the piston in the distal direction. When it is again desired to deflate the balloon or aspirate the treatment site, the physician merely has to slightly rotate the knob 40 until the main plunger is inappropriate alignment with the opening 54 in the flange plate 52 and pulling back on the knob 40 or knob 48.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. An inflation/deflation syringe apparatus for a balloon catheter for selectively injecting and withdrawing a fluid from a balloon catheter, comprising in combination:
    (a) a tubular housing having a proximal end and a distal end;
    (b) a tubular syringe disposed within said housing, said syringe including a cylindrical chamber containing a reciprocally movable piston member and having a fluid outlet proximate said distal end of said housing connectable to a balloon catheter;
    (c) an elongated shaft of generally circular cross-section connected at one end to said piston and having screw threads formed on a predetermined portion of the external surface thereof;

(d) a tubular main plunger rod coaxially disposed about said elongated shaft and having screw threads formed on a predetermined portion of the internal surface of said tubular plunger rod with which said screw threads on said elongated shaft engage, said tubular main plunger extending outwardly from said proximal end of said tubular housing through a non-circular opening therein of a predetermined shape, said tubular main plunger having a plurality of axially-spaced, parallel grooves formed in the external surface thereof along its length and having a cross-sectional shape corresponding to the shape of said non-circular opening, slight rotation of said tubular main plunger causing said tubular main plunger to become locked against axial movement relative to said housing by engagement of one of said grooves with the surface surrounding said non-circular opening; and (e) a knob secured to the proximal end of said elongated shaft for facilitating simultaneous axial displacement of said elongated shaft and said main plunger rod when said main plunger rod is in a predetermined aligned disposition relative to said non-circular opening and rotation of said elongated shaft within said main plunger shaft.

2. The inflation/deflation device of claim 1 wherein said housing includes an opening through which the longitudinal position of said piston within said cylindrical chamber can be viewed.

3. The inflation/deflation device of claim 1 and further including a pressure gauge and means for mounting said pressure gauge on said housing in fluid communication with said fluid outlet.

4. The inflation/deflation device as in claim 1 and further including an end-cap member secured to said proximal end of said housing, said end-cap member having radially projecting finger grips.

5. The inflation/deflation device as in claim 1 and further including an enlargement of generally circular cross-section on the exterior surface of said main plunger for facilitating the gripping thereof.

* * * * *